United States Patent
Gao et al.

(10) Patent No.: US 6,740,641 B2
(45) Date of Patent: May 25, 2004

(54) SUGAR DERIVATIVES OF HYDROMORPHONE, DIHYDROMORPHINE AND DIHYDROMORPHINE, COMPOSITIONS THEREOF AND USES FOR TREATING OR PREVENTING PAIN

(75) Inventors: Feng Gao, Stamford, CT (US); Jahanara Miotto, Carmel, NY (US)

(73) Assignee: Euro-Celtique, S.A. (LU)

( * ) Notice: Subject to any disclaimer, the term of this patent is extended or adjusted under 35 U.S.C. 154(b) by 0 days.

(21) Appl. No.: 10/199,526

(22) Filed: Jul. 22, 2002

(65) Prior Publication Data

US 2003/0050257 A1 Mar. 13, 2003

Related U.S. Application Data

(60) Provisional application No. 60/307,845, filed on Jul. 27, 2001.

(51) Int. Cl.$^7$ .................... A01N 43/04; C07D 471/00; C07D 489/00; C07D 491/00
(52) U.S. Cl. .................. 514/27; 514/281; 514/282; 546/44; 546/45; 546/46; 424/78.29
(58) Field of Search .................. 514/27, 281, 282, 514/25; 546/44, 45, 46; 424/78.29

(56) References Cited

FOREIGN PATENT DOCUMENTS

| EP | 0 324 212 A1 | 7/1989 | |
|---|---|---|---|
| EP | 816375 A1 * | 1/1998 | ........... C07H/17/02 |
| WO | WO 93/05057 * | 3/1993 | |
| WO | WO 97/21416 | 7/1997 | |
| WO | WO 98/54196 | 12/1998 | |

OTHER PUBLICATIONS

Mulder, Gerard J., Pharmacological Effects of Drug Conjugates: Is Morphine 6–glucuronide an Exception? TiPS, vol. 13, Aug. 1992, pp. 302–304.*

K. Oguri et al., "Synthesis and Analgesic Effect of Normorphine–3–and –6–glucuronides", *Chem. Pharm. Bull., 37*:955–957 (1988).
Carrupt et al., "Morphine 6–Glucuronide and Morphine 3–Glucuronide as Molecular Chameleons with Unexpected Lipophilicity", *J. Med. Chem. 34*:1272–1275 (1991).
Yohimura et al., "The Synthesis of Codeine and Morphine Glucuronides", *Tetrahedron Lett.* 483–486 (1968).
Budavari et al., *The Merck Index*, 758 (No. 4467) (12 ed. 1996).
Budavari et al., *The Merck Index*, 760 (No. 4474) (12 ed. 1996).
T. Reisine and G. Pasternak, "Opioid Analgesics and Antagonists" in *Goodman and Gilman's The Pharmacological Basis of Therapeutics*, 521–555 (9th ed. 1996).
R. Twycross, "Opioids" in Textbook of Pain, 943–955 (3$^{rd}$ ed. 1994).
G.J. Mulder, "Pharmacological Effects of Drug Conjugates: is Morphine 6–glucuronide an Exception?" *Trends in Pharmacol. Sci., 13*(8):302–304 (1992).
Osborne et al., "Analgesic Activity of Morphine–6–Glucuronide," *The Lancet* 828 (1988).
M. Zheng et al., "Hydromorphone metabolites: isolation and identification from pooled urine samples of a cancer patient," *Xenobiotica, 32*(5):427–439 (2002).

* cited by examiner

Primary Examiner—James O. Wilson
Assistant Examiner—Traviss C. McIntosh, III
(74) Attorney, Agent, or Firm—Jones Day

(57) ABSTRACT

Glucoside and glucuronide derivatives of hydromorphone, dihydromorphine, and dihydroisomorphine and pharmaceutically acceptable salts thereof; pharmaceutical compositions comprising a glucoside or glucuronide derivative of hydromorphone, dihydromorphine, or dihydroisomorphine or a pharmaceutically acceptable salt thereof; and methods for treating or preventing pain in a patient comprising administering to a patient in need thereof a glucoside or glucuronide derivative of hydromorphone, dihydromorphine, or dihydroisomorphine or a pharmaceutically acceptable salt thereof are disclosed.

51 Claims, No Drawings

SUGAR DERIVATIVES OF HYDROMORPHONE, DIHYDROMORPHINE AND DIHYDROMORPHINE, COMPOSITIONS THEREOF AND USES FOR TREATING OR PREVENTING PAIN

This application claims the benefit of U.S. Provisional Application No. 60/307,845, filed Jul. 27, 2001, which is incorporated herein by reference in its entirety.

1. FIELD OF THE INVENTION

The present invention relates to glucoside and glucuronide derivatives of hydromorphone, dihydromorphine, and dihydroisomorphine and pharmaceutically acceptable salts thereof; pharmaceutical compositions comprising glucoside or glucuronide derivatives of hydromorphone, dihydromorphine, or dihydroisomorphine or a pharmaceutically acceptable salt thereof; and methods for treating or preventing pain in a patient comprising administering to a patient in need thereof a glucoside or glucuronide derivative of hydromorphone, dihydromorphine, or dihydroisomorphine or a pharmaceutically acceptable salt thereof.

2. BACKGROUND OF THE INVENTION

Morphine and its known derivatives are opiates, which have pain-relief properties and are therefore useful in the treatment of chronic and acute pain in humans and other mammals. For example, morphine, hydromorphone, diamorphone, and oxymorphone are widely used as analgesic agents to control pain. Other commonly used, but more mildly acting, analgesics include codeine, dihydrocodeine, and nalbuphine.

Morphine was first isolated in 1806 and remains an important drug for treatment of moderate to severe pain, such as pain caused by cancer or surgery (T. Reisine and G. Pasternak, Opioid Analgesics and Antagonists, in Goodman and Gilman's The Pharmacological Basis of Therapeutics 521 (9th ed. 1996)). Although highly effective for relieving pain, presently used opiates may cause side effects (Id. at 536). In addition, the responses of individual patients to different opioids-purified alkaloids isolated from crude opium—can vary dramatically (Id. at 537). The mechanisms underlying this variation are not well understood (Id.). Furthermore, each opioid has a different potency, duration of action, and solubility (R. Twycross, Opioids, in Textbook of Pain, 953–955 (3rd ed. 1994)).

Morphine and other clinically used opioids exert their analgesic effect by binding to neuronal opiod receptors. Neuronal opioid receptors are distributed throughout the nervous system and classified as mu ($\mu$), kappa ($\kappa$) and delta ($\delta$) receptors. Each receptor class has a different binding affinity for each particular opioid. Opioid receptors work by activating an intracellular signaling pathway that decreases cyclic AMP, increases potassium efflux, and decreases calcium influx, thereby decreasing release of neurotransmitters (such as substance P) that are involved in the transmission of pain signals. Each receptor class achieves this effect using a different G-protein for signal transduction.

When bound to a particular ligand, each opioid-receptor class exerts a particular therapeutic effect. Ligand-bound mu receptors provide analgesia and euphoria. But ligand-bound kappa receptors are associated with paroxysm and diuresis and ligand-bound delta receptors are associated with dysphoria. Thus, opioids that bind selectively to mu receptors are preferable pain killers, since they avoid the undesirable side effects that result from binding to delta and kappa receptors. Morphine and other opioids can be selective mu-receptors binders, but only at low doses. Accordingly, there is a clear need in the art for mu-receptor binders that are more selective than morphine and other clinically used opioids, that have a higher therapeutic index for analgesia than morphine and other clinically used opioids, or that can be administered at doses larger than those for morphine and other clinically used opioids.

It is also known that glycoconjugates of opiates can exert pharmacological effects. For example, morphine-6-glucuronide, a glycoconjugate metabolite of morphine, is a more potent analgesic than morphine and morphine-3-glucuronide (G. J. Mulder, Trends in Pharmacol. Sci., 13(8) :302–304 (1992) and Osborne et al., The Lancet 828 (1988)).

WO 97/21416 discloses a series of carbohydrate derivatives of biologically active opiates having at least one residue of carbohydrate per opiate molecule.

WO 98/54196 discloses sugar derivatives of opiate compounds comprising at least one sugar residue coupled with at least one opiate residue through an $\alpha$-glycosidic bond. The sugar derivatives of opiate compounds allegedly have analgesic properties.

WO 93/05057 discloses glucuronides of 4,5-epoxymorphinanes that are allegedly useful as analgesic agents and methods for their preparation.

M. Zheng et al., Xenobiotica, 32(5):427–439 (2002) discloses particular metabolites of hydromorphone.

There remains a clear need in the art for improved compounds, particularly mu-receptor-selective compounds, and methods for using them to treat or prevent pain.

Citation or identification of any reference in Section 2 of the application is not an admission that such reference is available as prior art to the application.

3. SUMMARY OF THE INVENTION

The present invention relates to 3-O-glucosylhydromorphone and pharmaceutically acceptable salts thereof.

The present invention also relates to 3-O-glucosyldihydroisomorphine and pharmaceutically acceptable salts thereof.

The present invention further relates to 6-O-glucosyldihydroisomorphine and pharmaceutically acceptable salts thereof.

The present invention still further relates to 3-O-glucosyldihydromorphine and pharmaceutically acceptable salts thereof.

The present invention still further relates to 6-O-glucosyldihydromorphine and pharmaceutically acceptable salts thereof.

The present invention still further relates to nordihydromorphine-3-glucuronide and pharmaceutically acceptable salts thereof.

The present invention still further relates to nordihydroisomorphine-3-glucuronide and pharmaceutically acceptable salts thereof.

The present invention still further relates to norhydromorphone-3-glucuronide and pharmaceutically acceptable salts thereof.

3-O-Glucosylhydromorphone, 3-O-glucosyldihydroisomorphine, 6-O-glucosyldihydroisomorphine, 3-O-glucosyldihydromorphine, 6-O-glucosyldihydromorphine, nordihydromorphine-3-glucuronide, nordihydroisomorphine-3-glucuronide, norhydromorphone-3-glucuronide, or pharmaceutically acceptable salts thereof (a "compound of the invention") is useful for treating or preventing pain in a patient.

In one embodiment, the compounds of the invention are in isolated and purified form.

The invention also relates to pharmaceutical compositions comprising an effective amount a compound of the invention and a pharmaceutical acceptable carrier or vehicle. These compositions are useful for treating or preventing pain in a patient.

The invention further relates to methods for treating or preventing pain in a patient comprising administering to a patient in need of such treatment or prevention an effective amount of a compound of the invention.

The present invention may be understood more fully by reference to the following detailed description and illustrative examples, which are intended to exemplify non-limiting embodiments of the invention.

4. DETAILED DESCRIPTION OF THE INVENTION

4.1 Definitions

3-O-Glucosylhydromorphone has the structural formula (I):

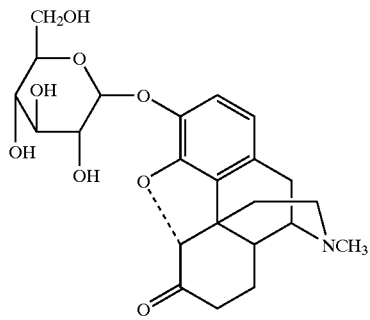

(I)

3-O-Glucosyldihydroisomorphine has the structural formula (II):

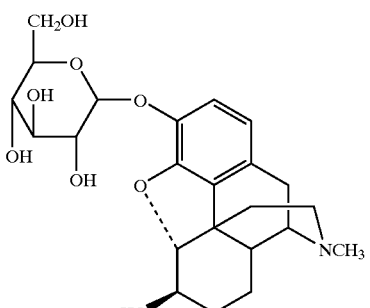

(II)

6-O-Glucosyldihydroisomorphine has the structural formula (III):

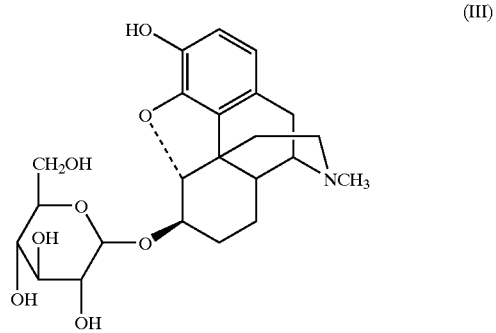

(III)

3-O-Glucosyldihydromorphine has the structural formula (IV):

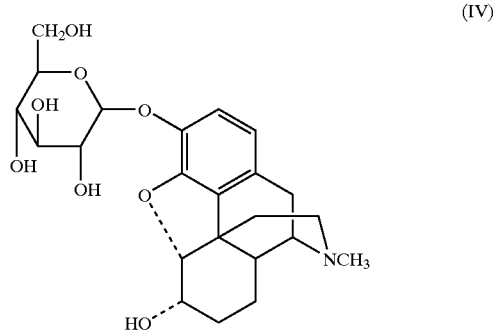

(IV)

6-O-Glucosyldihydromorphine has the structural formula (V):

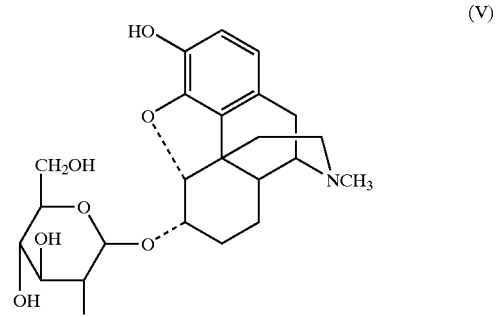

(V)

Nordihydromorphine-3-glucuronide has the structural formula (VI):

(VI)

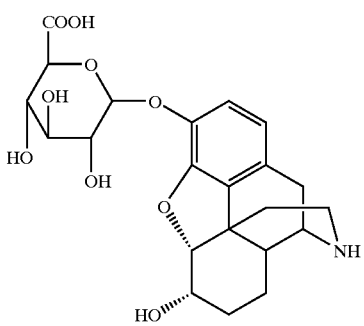

Nordihydroisomorphine-3-glucuronide has the structural formula (VII):

(VII)

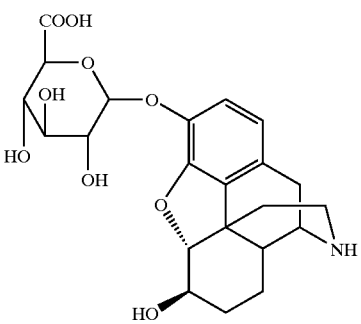

Norhydromorphone-3-glucuronide has the structural formula (VII):

(VIII)

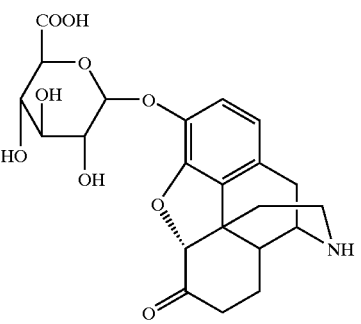

As used herein, the term "isolated and purified" means isolated from another component or from other components of a naturally occurring source (such as a plant or animal cell, including a hepatocyte; cell culture; tissue; in vivo fluid including intracellular and extracellular fluid, including blood and plasma; and ex vivo fluid including sputum, urine, sweat, semen, menstrual fluid, and milk) or from a synthetic organic chemical reaction mixture, and processed through one or more purifying steps that separate the compound of the invention from other molecules associated with it. When isolated and purified, the compound of the invention is at least about 95% pure. In one embodiment, the compound of the invention is at least about 98% pure. In another embodiment, the compound of the invention is at least about 99% pure.

A "patient" is an animal, including, but not limited to, an animal such a cow, monkey, horse, sheep, pig, chicken, turkey, quail, cat, dog, mouse, rat, rabbit, and guinea pig. In one embodiment the animal is a mammal. In another embodiment the animal is a human.

The phrase "pharmaceutically acceptable salt," as used herein is a salt formed from an acid and the basic nitrogen group of one of the compounds of formula (I)–(V). Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, β-toluenesulfonate, and pamoate (i.e., 1,1'-methylene-bis-(2-hydroxy-3-naphthoate)) salts. The term "pharmaceutically acceptable salt" also refers to a salt prepared from the acidic group of the glucoronide residue and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

The phrase "treatment of pain" or "treating pain" refers to an amelioration of pain or the cessation of pain in a patient.

The phrase "prevention of pain" or "preventing pain" refers to an avoidance of the onset of pain in a patient. The phrase "α-glycoside" and "α-gluconoride" as used herein means that the non-sugar (aglycon) portion of the compounds of the invention is on the opposite side of the glucoside as its —CH$_2$OH or —COOH group, respectively.

The phrase "β-glycoside" and "β-gluconoride" as used herein means that the non-sugar (aglycon) portion of the compounds of the invention is on the same side of the glucoside as its —CH$_2$OH or —COOH group, respectively.

4.2 The Compounds of the Invention

Applicants have discovered that the compounds of the invention are surprisingly and unexpectedly mu-receptor selective and, accordingly, are advantageous over traditional analgesic agents that competitively bind to kappa and delta receptors. Accordingly, the compounds of the invention are particularly useful for treating or preventing pain.

In one embodiment, the compounds of the invention are in isolated and purified form.

In another embodiment, the compounds of the invention are β-glycosides or β-glucoronides.

In another embodiment, the compounds of the invention are α-glycosides or α-glucoronides.

4.2.1 Synthesis

The compounds of the invention can be prepared by any known or later developed method for forming O-glycosidic or gluconoridic bonds. Representative methods include, but are not limited to, the Koenigs-Knorr procedure (W. Koenigs et al., *Ber.* 34:965 (1901)), wherein an acetylglycosyl halide is reacted with an alcohol or phenol in the presence of silver carbonate or silver oxide (See, e.g., Evans et al., 6 *Advances in Carbohydrate Chemistry* 41 (1951)) and the Helferich procedure (B. Helferich et al., *Ber.* 66:378 (1933)), wherein an acetylated sugar is heated with a phenol or an alcohol in the presence of zinc chloride or β-toluenesulfonic acid (See, e.g., W. W. Pigman, *The Cabohydrates* 98 (1957)).

Useful methods for obtaining 3-O-Glucosylhydromorphone, 3-O-glucosyldihydroisomorphine, 6-O-glucosyldihydroisomorphine, 3-O-glucosyldihydromorphine, and 6-O-glucosyldi- hydromorphine generally involve: reacting hydromorphone, dihydromorphine, or dihydroisomorphine, optionally monoprotected and having a free hydroxyl group, with an optionally protected, activated sugar, typically in the presence of a catalyst; and subsequently removing the protecting group(s).

Useful methods for obtaining nordihydromorphine-3-glucuronide, nordihydroisomorphine-3-glucuronide, and norhydromorphone-3-glucuronide generally involve: demethylating the nitrogen of hydromorphone, dihydromorphine, or dihydroisomorphine; protecting the nitrogen of hydromorphone, dihydromorphine, or dihydroisomorphine; reacting the nitrogen protected hydromorphone, dihydromorphine, or dihydroisomorphine, optionally monoprotected on one of the oxygens and having a free hydroxyl group, with an optionally protected, activated sugar, typically in the presence of a catalyst; and then removing the nitrogen protecting group and the optional oxygen protecting group.

Useful catalysts are, for example, Ag+ and Hg+compounds, Lewis acids, and bases.

Useful Ag$^+$ or Hg$^{++}$ compounds include, but are not limited to, silver triflate, silver carbonate, and mercuric cyanide.

Useful Lewis acids include, but are not limited to, aluminum halides, alkylaluminum halides, boron halides, tin halides, titanium halides, lead halides, zinc halides, iron halides, gallium halides, arsenic halides, copper halides, cadmium halides, mercury halides, antimony halides, and the like. Preferred Lewis acids include aluminum trichloride, aluminum tribromide, trimethylaluminum, boron trifluoride, boron trichloride, zinc dichloride, titanium tetrachloride, tin dichloride, tin tetrachloride, and mixtures thereof.

Useful bases include, but are not limited to, hydroxides such as LiOH and organic tertiary amines such as triethylamine and pyridine.

Protecting groups that are useful for protecting the nitrogen atom of norhydromorphone, nordihydromorphine and nordihydroisomorphine are disclosed in T. W. Greene, *Protective Groups in Organic Synthesis* 218–287 (1981). In one embodiment, the protecting group is removable under nonacidic conditions. In other embodiments, the protecting group is a t-butoxycarbonyl group (R. S. Lott et al., *J. Chem Soc., Chem. Commun.* 495 (1979)); a benzyloxycarbonyl group (M. Bergmann et al., *Ber.* 65:1192 (1932)); an allyl group (J. A. Montgomery et al., *J. Org. Chem.* 30:3235 (1965)) or a benzyl group (W. H. Hartung et al., 7 *Org. Reactions* 263 (1965)).

The glycosidic-bond-forming reaction is typically carried out in an organic solvent. Illustrative organic solvents include, but are not limited to, acetonitrile, methanol, and methylene chloride. Typically, the reaction temperature is from about −78° C. to the reflux temperature of the solvent.

In one embodiment, the reaction temperature is from about −40° C. to about room temperature.

4.2.2 Synthesis of 3-O-Glucosylhydromorphone

3-O-Glucosylhydromorphone can be obtained using conventional organic synthesis, or via the following illustrative method shown in Scheme A.

Scheme A:

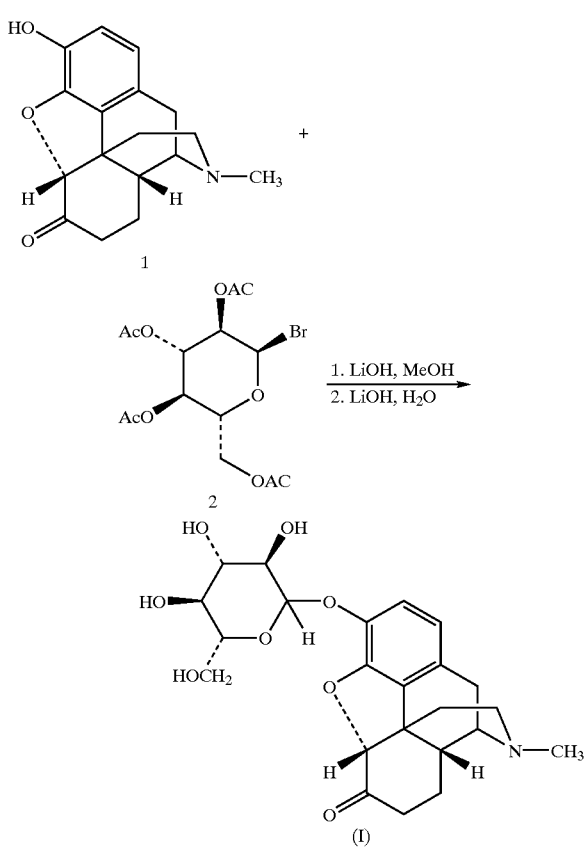

3-O-Glucosylhydromorphone (I) can be prepared by reacting 2,3,4,6-tetra-O-acetyl-α-D-glucopyranosyl bromide (2) with hydromorphone (1) in methanolic lithium hydroxide followed by reaction with aqueous lithium hydroxide.

4.2.3 Synthesis of 3-O-Glucosyldihydroisomorphine

3-O-Glucosyldihydroisomorphine can be obtained using conventional organic synthesis, or via the following illustrative method shown in Scheme B.

Scheme B:

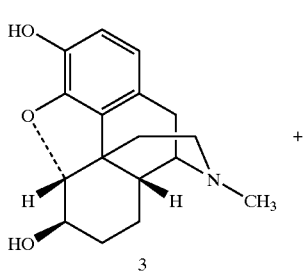

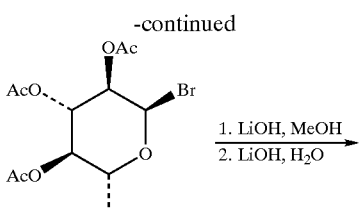

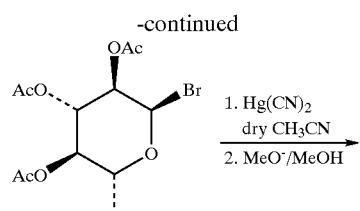

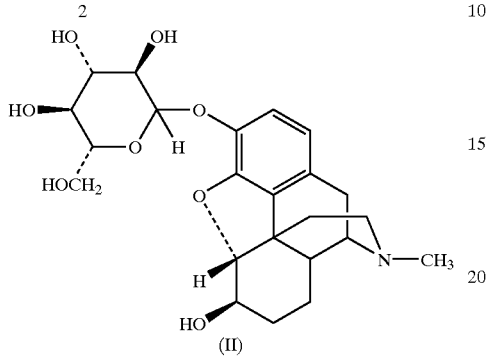

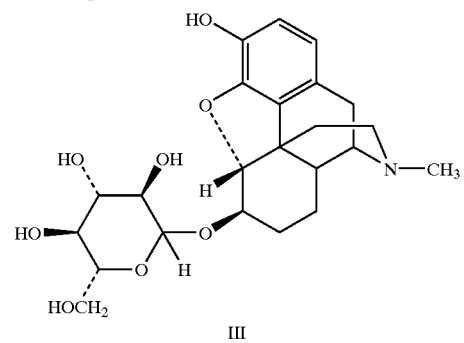

3-O-Glucosyldihydroisomorphine (II) can be prepared by reacting 2,3,4,6-tetra-O-acetyl-α-D-glucopyranosyl bromide (2) with dihydroisomorphine (3) in methanolic lithium hydroxide followed by reaction with aqueous lithium hydroxide.

Dihydroisomorphine (3) can be prepared from dihydromorphine using methods readily known to those of skilled in the art. For example, dihydromorphine can be reacted with β-toluenesulfonyl chloride to provide dihydromorphine-6-tosylate, which can be reacted with hydroxide ion to displace the tosylate and invert the stereochemistry of the hydroxyl group at the 6-position.

Dihydromorphine can be obtained by hydrogenating morphine, for example, using hydrogen and a carbon-palladium catalyst.

4.2.4 Synthesis of 6-O-Glucosyldihydroisomorphine

6-O-Glucosyldihydroisomorphine can be obtained using conventional organic synthesis or by the following illustrative method shown in Scheme C.

Scheme C:

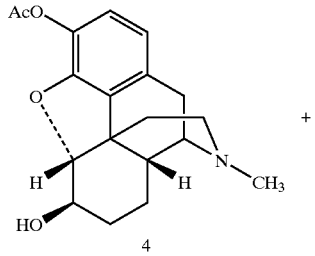

6-O-Glucosyldihydroisomorphine (III) can be prepared by reacting 2,3,4,6-tetra-O-acetyl-α-D-glucopyranosyl bromide (2) with 3-acetyl dihydroisomorphine (4) in dry acetonitrile in the presence of mercuric cyanide followed by removal of the acetyl protecting groups with sodium methoxide in methanol (See, e.g., P. Kovac et al., *Heterocycles* 36(4):697–708 (1995)).

3-Acetyl dihydroisomorphine (4) can be prepared from dihydroisomorphine using methods well known to those skilled in the art (See, e.g., L. H. Welsh, *J. Org. Chem.* 19:1409 (1954) and U.S. Pat. No. 6,046,313 to Scheinmann et al.).

Dihydroisomorphine can be prepared from dihydromorphine, both of which can be obtained using methods readily known to those skilled in the art and described above.

4.2.5 Synthesis of 3-O-Glucosyldihydromorphine

3-O-Glucosyldihydromorphine can be obtained using conventional organic synthesis or by the following illustrative method shown in Scheme D.

Scheme D:

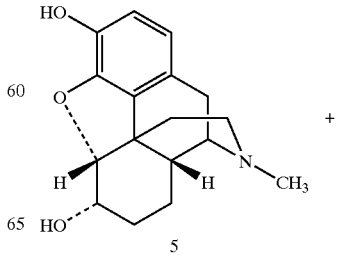

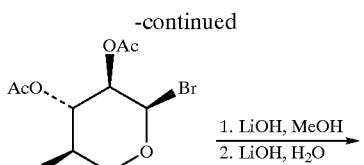

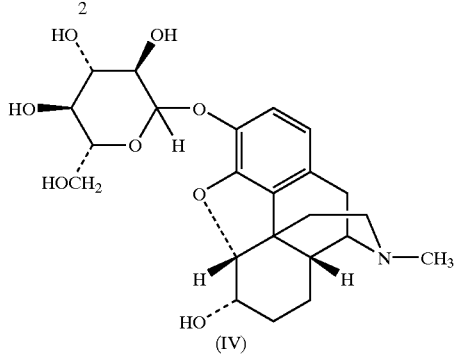

3-O-Glucosyldihydromorphine (IV) can be prepared by reacting 2,3,4,6-tetra-O-acetyl-α-D-glucopyranosyl bromide (2) with dihydromorphine (5) in methanolic lithium hydroxide followed by reaction with aqueous lithium hydroxide.

Dihydromorphine can be obtained using methods described above.

4.2.6 Synthesis of 6-O-Glucosyldihydromorphine

6-O-Glucosyldihydromorphine can be obtained using conventional organic synthesis or by the following illustrative method shown in Scheme E.

Scheme E:

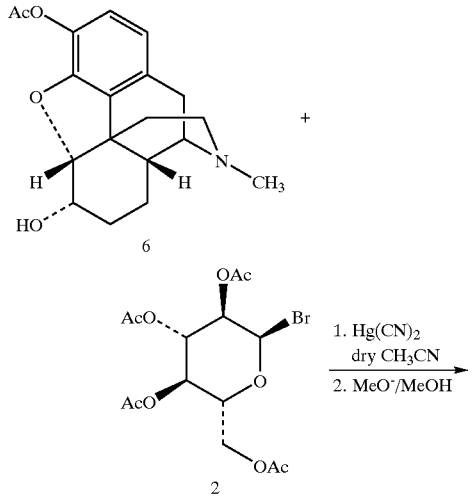

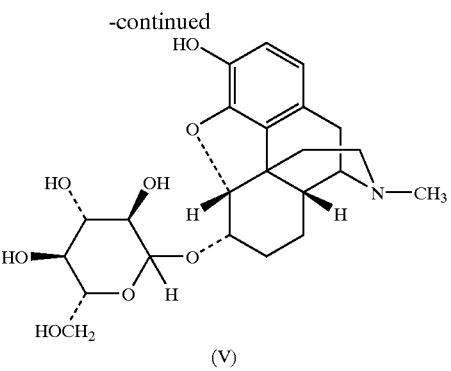

6-O-Glucosyldihydromorphine (V) can be prepared by reacting 2,3,4,6-tetra-O-acetyl-α-D-glucopyranosyl bromide (2) with 3-acetyl dihydromorphine (6) in dry acetonitrile in the presence of mercuric cyanide followed by removal of the acetyl protecting groups with sodium methoxide in methanol (see, e.g., P. Kovac et al., *Heterocycles* 36(4):697–708 (1995)).

3-Acetyl dihydromorphine (6) can be prepared from dihydromorphine using methods well known to those skilled in the art (See, e.g., L. H. Welsh, *J. Org. Chem.* 19:1409 (1954) and U.S. Pat. No. 6,046,313 to Scheinmann et al.).

Dihydromorphine can be obtained using methods described above.

4.2.7 Synthesis of Nordihydromorphine-3-Glucuronide

Nordihydromorphine can be obtained using conventional organic synthesis or by the following illustrative method shown in Scheme F.

Scheme F:

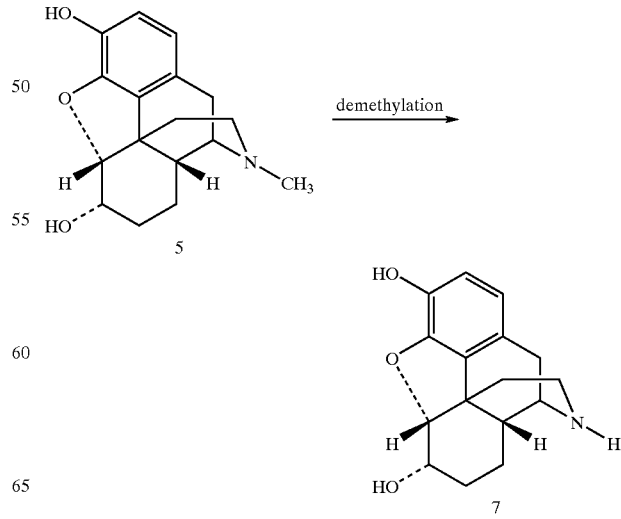

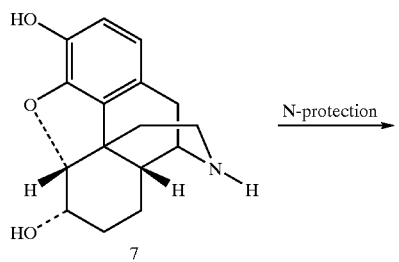

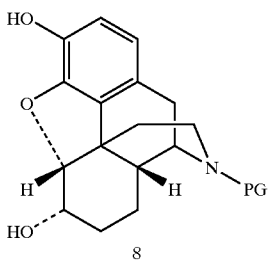

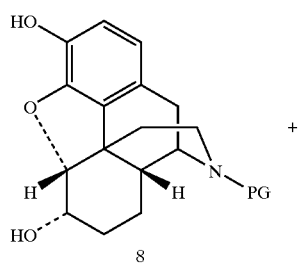

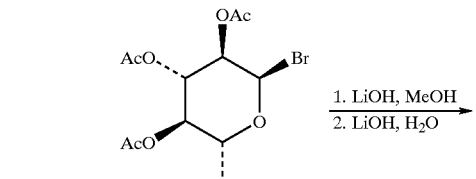

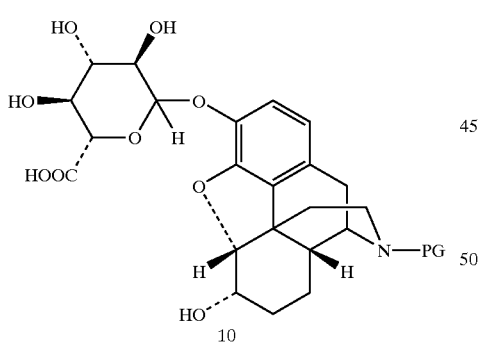

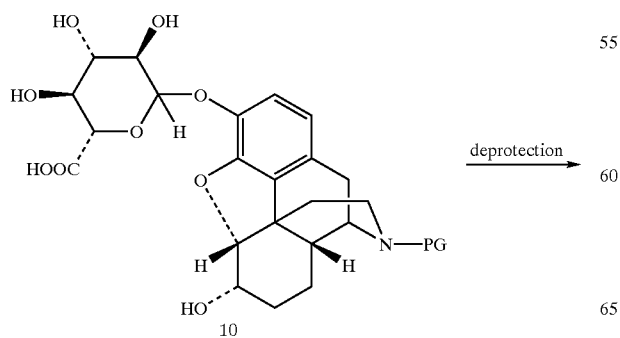

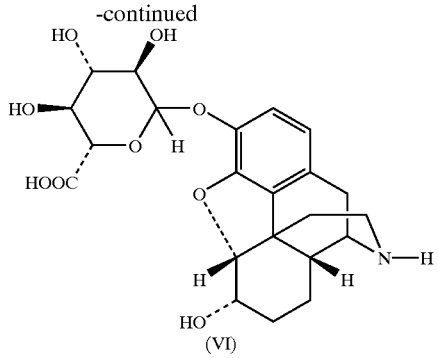

wherein PG is a nitrogen protecting group.

Nordihydromorphine-3-glucuronide (VI) can be prepared by demethylating dihydromorphine (5) using procedures well known to those skilled in the art (See, e.g., J. March, *Advanced Organic Chemistry, Reaction Mechanisms and Structure*, 4$^{th}$ ed. John Wiley & Sons, NY, 1992, p. 709 and K. Rice, *J. Org. Chem.*, 40:1850 (1975)) to provide nordihydromorphine (7). The nitrogen atom of nordihydromorphine (7) is then protected with a suitable protecting group as described above to provide an N-protected nordihydromorphine (8) and the N-protected nordihydromorphine (8) is reacted with 2,3,4-tri-O-acetyl-1α-bromo-1-deoxy-D-glucopyranuronic methyl ester (9) in methanolic lithium hydroxide followed by reaction with aqueous lithium hydroxide according to the procedure described in M. Zheng et al., *Xenobiotica* 19:(5) 427–439 (2002) to provide N-protected nordihydromorphine-3-glucuronide (10). The nitrogen protecting group of the N-protected nordihydromorphine-3-glucuronide (10) is then removed using procedures well known to those skilled in the art as described above to provide nordihydromorphine-3-glucuronide (VI).

Dihydromorphine can be obtained using methods described above.

4.2.8 Synthesis of Nordihydroisomorphine-3-Glucuronide

Nordihydroisomorphine-3-glucuronide can be obtained using conventional organic synthesis or by the following illustrative method shown in Scheme G.

Scheme G:

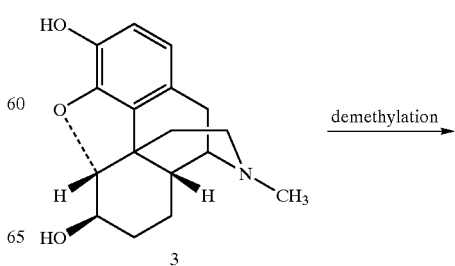

-continued

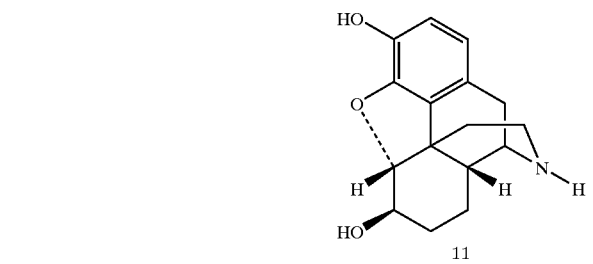
11

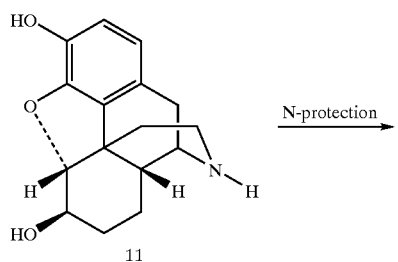
11

N-protection →

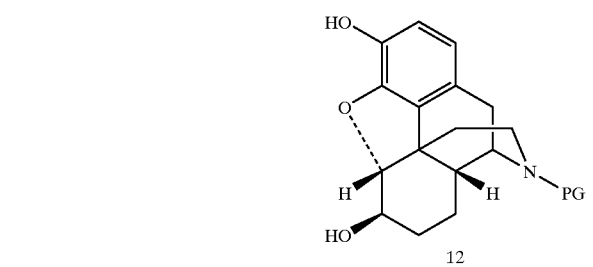
12

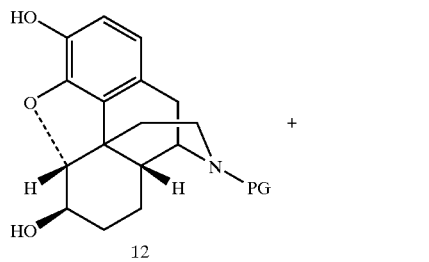
12

+

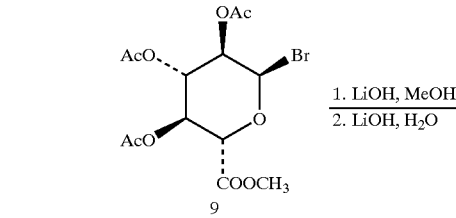
9

1. LiOH, MeOH
2. LiOH, H₂O

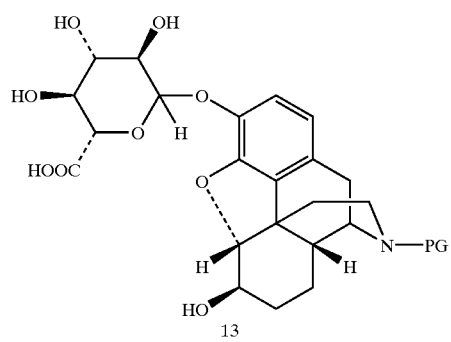
13

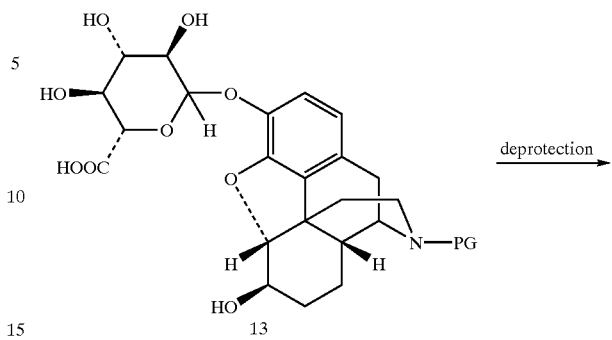
13 deprotection →

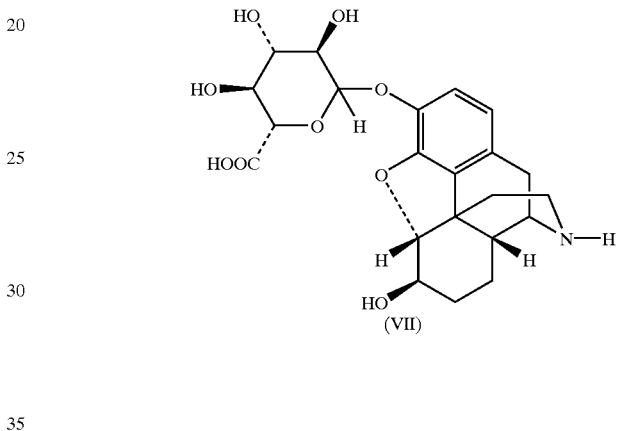
(VII)

wherein PG is a nitrogen protecting group.

Nordihydroisomorphine-3-glucuronide (VII) can be prepared by demethylating dihydroisomorphine (3) using procedures well known to those skilled in the art (See, e.g., J. March, *Advanced Organic Chemistry, Reaction Mechanisms and Structure*, 4$^{th}$ ed. John Wiley & Sons, NY, 1992, p. 709; and K. Rice, *J. Org. Chem.*, 40:1850 (1975)) to provide nordihydroisomorphine (11). The nitrogen atom of nordihydroisomorphine (11) is then protected with a suitable protecting group as described above to provide an N-protected nordihydroisomorphine (12) and the N-protected nordihydroisomorphine (12) is reacted with 2,3,4-tri-O-acetyl-1α-bromo-1-deoxy-D-glucopyranuronic methyl ester (9) in methanolic lithium hydroxide followed by reaction with aqueous lithium hydroxide according to the procedure described in M. Zheng et al., *Xenobiotica* 19:(5) 427–439 (2002) to provide N-protected nordihydromorphine-3-glucuronide (13). The nitrogen protecting group of the N-protected nordihydromorphine-3-glucuronide (13) is then removed using procedures well known to those skilled in the art as described above to provide nordihydromorphine-3-glucuronide (VII).

Dihydroisomorphine can be obtained using methods described above.

4.2.8 Synthesis of Norhydromorphone-3-Glucuronide

Norhydromorphone-3-glucuronide, can be obtained using conventional organic synthesis or by the following illustrative method shown in Scheme H.

Scheme H:

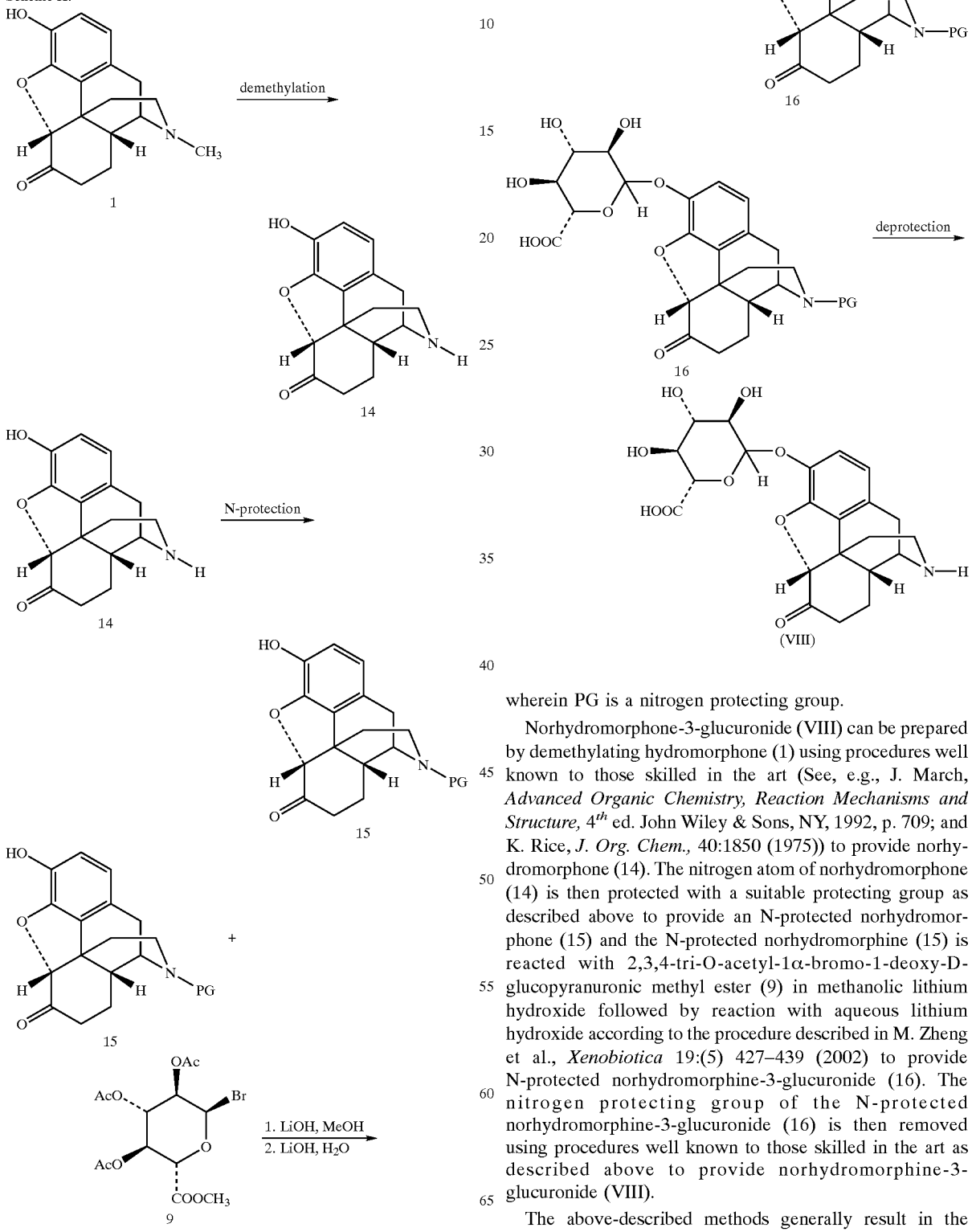

wherein PG is a nitrogen protecting group.

Norhydromorphone-3-glucuronide (VIII) can be prepared by demethylating hydromorphone (1) using procedures well known to those skilled in the art (See, e.g., J. March, *Advanced Organic Chemistry, Reaction Mechanisms and Structure*, 4th ed. John Wiley & Sons, NY, 1992, p. 709; and K. Rice, *J. Org. Chem.*, 40:1850 (1975)) to provide norhydromorphone (14). The nitrogen atom of norhydromorphone (14) is then protected with a suitable protecting group as described above to provide an N-protected norhydromorphone (15) and the N-protected norhydromorphine (15) is reacted with 2,3,4-tri-O-acetyl-1α-bromo-1-deoxy-D-glucopyranuronic methyl ester (9) in methanolic lithium hydroxide followed by reaction with aqueous lithium hydroxide according to the procedure described in M. Zheng et al., *Xenobiotica* 19:(5) 427–439 (2002) to provide N-protected norhydromorphine-3-glucuronide (16). The nitrogen protecting group of the N-protected norhydromorphine-3-glucuronide (16) is then removed using procedures well known to those skilled in the art as described above to provide norhydromorphine-3-glucuronide (VIII).

The above-described methods generally result in the formation of a mixture of the α- and β-glycoside of 3-O- glucosylhydromorphone, 3-O-glucosyldihydroisomorphine, 6-O-glucosyldihydroisomorphine, 3-O-glucosyl- dihydromorphine or 6-O-glucosyldihydromorphine, and the α- and β-glucuronide of nordihydromorphine-3-glucuronide, nordihydroisomorphine-3-glucuronide, or norhydromorphone-3-glucuronide, with the β-glycoside or β-glucuronide form predominating. Methods for obtaining α-glycosides are well known (See, e.g., I. Rukham et al., *Tetrahetron Lett.* 41:6889–6892 (2000) and I. Rukham et al., Tetrahedron Lett. 57:1083–1092 (2001)) and can be used to obtain the α-glycoside form of 3-O-glucosylhydromorphone, 3-O-glucosyldihydroisomorphine, 6-O-glucosyldihydroisomorphine, 3-O-glucosyldihydromorphine, and 6-O-glucosyldihydromorphine or the α-glucoronide form of nordihydromorphine-3-glucuronide, nordihydroisomorphine-3-glucuronide, and norhydromorphone-3-glucuronide.

The α- and β-glycosides of 3-O-glucosylhydromorphone, 3-O-glucosyldihydroisomorphine, 6-O-glucosyl-dihydroisomorphine, 3-O-glucosyldihydromorphine, and 6-O-glucosyldihydromorphine and the α- and β-glucorinides of nordihydromorphine-3-glucuronide, nordihydroisomorphine-3-glucuronide, and norhydromorphone-3-glucuronide are separable using conventional techniques, including silica-gel and high-performance liquid chromatography.

4.3 Therapeutic Uses for the Compounds of the Invention

The compounds of the invention are administered to a patient for the treatment or prevention of pain. In one embodiment the patient is a mammal. In another embodiment the patient is a human,. The compounds of the invention may be used to treat acute or chronic pain. For example, the compounds of the invention can be used for treating or preventing pain including, but are not limited to, cancer pain, central pain, labor pain, myocardial infarction pain, pancreatic pain, colic pain, post-operative pain, headache pain, muscle pain, and pain associated with intensive care. Advantageously, the compounds of the invention exhibit high selectivity for the mu opiod receptor and therefore avoid many of the side effects associated with other opiates that competitively bind to kappa and delta receptors.

4.4 Therapeutic/Prophylactic Administration and Compositions of the Invention Due to their activity, the compounds of the invention are advantageously useful in veterinary and human medicine. As described above, the compounds of the invention are useful for treating or preventing pain in a patient.

When administered to a patient, a compound of the invention can be administered as a component of a composition that optionally comprises a pharmaceutically acceptable carrier or vehicle. These compositions can be administered orally. The compositions can also be administered by any other convenient route, for example, by infusion or bolus injection, by absorption through epithelial or mucocutaneous linings (e.g., oral mucosa, rectal, and intestinal mucosa, etc.) and can be administered together with another biologically active agent. Administration can be systemic or local. Various known delivery systems, e.g., encapsulation in liposomes, microparticles, microcapsules and capsules, can be used to administer the compounds of the invention.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a compound of the invention into the bloodstream.

In specific embodiments, it may be desirable to locally administer the compounds of the invention. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce the compounds of the invention into the central nervous system by any suitable route, including intraventricular, intrathecal, and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, *Science* 249:1527–1533; Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.).

In yet another embodiment, the compounds of the invention can be delivered in a controlled-release system (see, e.g., Goodson, in Medical Applications of Controlled Release, supra, vol. 2, pp. 115–138 (1984)). Other controlled-release systems discussed in the review by Langer, 1990, *Science* 249:1527–1533 may be used. In one embodiment, a pump may be used (see Langer, supra; Sefton, 1987, *CRC Crit. Ref. Biomed. Eng.* 14:201; Buchwald et al., 1980, *Surgery* 88:507 Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled-release system can be placed in proximity of a target of the compounds of the invention, e.g., the spinal column or brain, thus requiring only a fraction of the systemic dose.

The present compositions can optionally comprise a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, mammals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable, or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating, and coloring agents may be used. When administered to a patient, the pharmaceutically acceptable vehicles are typically sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, propylene, glycol, water, ethanol, and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in *Remington's Pharmaceutical Sciences*, Alfonso R. Gennaro ed., Mack Publishing Co. Easton, Pa., 19th ed., 1995, pp. 1447 to 1676, incorporated herein by reference.

In a preferred embodiment, the compounds of the invention are formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharin, cellulose and magnesium carbonate. Such vehicles are typically of pharmaceutical grade.

In another embodiment, the compounds of the invention can be formulated for intravenous administration. Typically, compositions for intravenous administration comprise sterile isotonic aqueous buffer. Where necessary, the compositions may also include a solubilizing agent. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compounds of the invention are to be administered by infusion, it can be dispensed, for example, with an infusion bottle containing sterile pharmaceutical grade water or saline. Where the compounds of the invention are administered by injection, an ampoule of sterile water for injection or saline can be provided so that the ingredients may be mixed prior to administration.

The amount of a compound of the invention that will be effective in the treatment or prevention of pain will depend on the nature of the disorder or condition causing the pain, and can be determined by standard clinical techniques. In addition, in vitro or in vivo assays can optionally be employed to help identify optimal dosage ranges. The precise dose to be employed will also depend on the route of administration, and the seriousness of the pain, and should be decided according to the judgment of the practitioner and each patient's circumstances. Suitable dosages, however, range from 50 micrograms to more than 2500 milligrams every 4 hours, although typically 100 mg or less. In one embodiment, the dosage is about 0.01 milligram to about 100 milligrams of a compound of the invention every four hours. In another embodiment the dosage is about 0.025 milligrams to 50 milligrams every four hours. In yet another embodiment the dosage is about 0.02 milligrams to about 20 milligrams every four hours. The dosage amounts described herein refer to total amounts administered; that is, if more than one compound of the invention is administered, the preferred dosages correspond to the total amount administered.

The invention also provides pharmaceutical packs or kits comprising one or more vessels containing a compound of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The compounds of the invention are can be assayed in vitro or in vivo for the desired therapeutic or prophylactic activity, prior to use in humans. Animal model systems can be used to demonstrate safety and efficacy.

Other methods will be known to those skilled in the art and are within the scope of the invention.

The invention encompasses methods for treating or preventing pain in a patient, comprising administering to a patient in need thereof an effective amount of a compound of the invention and another therapeutic agent. In certain embodiments of the present invention, the compounds of the invention can be used in combination with at least one other therapeutic agent.

The other therapeutic agent includes, but is not limited to, an opioid agonist, a non-opioid analgesic, a non-steroid anti-inflammatory agent, an antimigraine agent, a Cox-II inhibitor, an antiemetic, a β-adrenergic blocker, an anticonvulsant, an antidepressant, a Ca2+-channel blocker, or an anticancer agent.

Effective amounts of the other therapeutic agents are well known to those skilled in the art. However, it is well within the skilled artisan's purview to determine the other therapeutic agent's optimal effective-amount range. In one embodiment of the invention where another therapeutic agent is administered to an animal, the effective amount of the compound of the invention is less than its effective amount would be where the other therapeutic agent is not administered. In this case, without being bound by theory, it is believed that the compound of the invention and the other therapeutic agent act synergistically to treat or prevent pain.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, pirprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic-Antipyretic and Anti-inflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9$^{th}$ ed 1996) and Glen R. Hanson, *Analgesic, Antipyretic and Anti-Inflammatory Drugs* in Remington: *The Science and Practice of Pharmacy Vol II* 1196–1221 (A. R. Gennaro ed. 19th ed. 1995) which are hereby incorporated by reference in their entireties.

Suitable Cox-II inhibitors and 5-lipoxygenase inhibitors, as well as combinations thereof, are described in U.S. Pat. No. 6,136,839, which is hereby incorporated by reference in its entirety. Cox-II inhibitors include, but are not limited to, rofecoxib and celecoxib.

Examples of useful antimigraine agents include, but are not limited to, alpiropride, dihydroergotamine, dolasetron, ergocornine, ergocorninine, ergocryptine, ergot, ergotamine, flumedroxone acetate, fonazine, lisuride, lomerizine, methysergide oxetorone, pizotyline, and mixtures thereof.

The other therapeutic agent can also be an agent useful for reducing any potential side effects of a compound of the invention. For example, the other therapeutic agent can be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful Ca2+-channel blockers include, but are not limited to, bepridil, clentiazem, diltiazem, fendiline, gallopamil, mibefradil, prenylamine, semotiadil, terodiline, verapamil, amlodipine, aranidipine, bamidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexiline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alfa-2a, interferon alfa-2b, interferon alfa-n1, interferon alfa-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin;

hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein α-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

The compound of the invention and the other therapeutic agent can act additively or synergistically. In a preferred embodiment, a composition comprising a compound of the invention is administered concurrently with the administration of another therapeutic agent, which can be part of the same composition or in a different composition from that comprising the compound of the invention. In another embodiment, a composition comprising a compound of the invention is administered prior to or subsequent to administration of another therapeutic agent.

5. EXAMPLES

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Example 1

3-O-β-Glucosyldihydroisomorphine 2,3,4,6-tetra-O-acetyl-α-D-glucopyranosyl bromide (1.19 g, 3.0 mmol) was added in one portion to a stirred solution of LiOH·H$_2$O (0.15 g, 3.5 mmol) and dihydroisomorphine (1.0 g, 3.0 mmol) in dry methanol (10 mL) at room temperature. The resulting mixture was stirred for 1 hr, and a solution of LiOH·H$_2$O (0.42 g, 10.0 mmol) in water (10 mL) was added dropwise to the mixture, which was allowed to stir for an additional 3 hr. The resulting suspension was acidified to pH 7 with acetic acid (0.5 mL) and 20 mL of chloroform was added. The resulting precipitate was removed from the suspension by filtration and washed twice with 20 mL of chloroform/ethanol, providing a crude product. The crude product was dissolved in 70% aqueous methanol (25 mL), allowed to recrystallize overnight at −10° C., filtered, washed with ethanol (20 mL) and acetone (20 mL), and dried under reduced pressure (10 mm Hg, 50° C.) to provide 0.52 g (45%) of 3-O-β-glucosyl-dihydroisomorphine as a white solid.

Example 2

3-β-O-Glucosyldihydromorphine 2,3,4,6-Tetra-O-acetyl-α-D-glucopyranosyl bromide (1.20 g, 3.0 mmol) was added in one portion to a stirred solution of LiOH·H$_2$O (0.15 g, 3.5 mmol) and dihydromorphine (1.0 g, 3.0 mmol) in dry methanol (10 mL) at room temperature. The resulting mixture was stirred for 1 hr, a solution of LiOH·H$_2$O (0.42 g, 10.0 mmol) in water (10 mL) was added dropwise to the mixture, and the mixture allowed to stir for an additional 3 hr. The resulting suspension was acidified to pH 7 with acetic acid (0.5 mL) and 20 mL of chloroform was added. The resulting precipitate was removed by filtration and washed with ethanol (20 mL) following by acetone (20 mL), to provide a crude product. The crude product was dissolved in 50% aqueous methanol (12 mL), recrystallized at 0° C., filtered, and dried under reduced pressure (10 mm Hg, 50° C.) to provide 0.33 g (30%) of 3-O—β-glucosyldihydromorphine.

Example 3

3-β-O-Glucosyldihydromorphone 2,3,4,6-Tetra-O-acetyl-α-D-glucopyranosyl bromide (3.0 mmol) is added in one portion to a stirred solution of LiOH·H$_2$O (3.5 mmol) and dihydromorphone (3.0 mmol) in dry methanol (10 mL) at room temperature. The resulting mixture is stirred for 1 hr, and a solution of LiOH·H$_2$O (10.0 mmol) in water (10 mL) is added dropwise to the mixture, which is allowed to stir for an additional 3 hr. The resulting suspension is acidified to pH 7 with acetic acid (about 0.5 mL) and 20 mL of chloroform is added. The resulting precipitate is removed by filtration and washed with ethanol (20 mL) following by acetone (20 mL), to provide a crude product. The crude product is recrystallized, filtered, and dried under reduced pressure (10 mm Hg, 50° C.) to provide 3-O-β-glucosyldihydromorphone.

Example 4

6-P-O-Glucosyldihydromorphine

A mixture of 3-acetyl dihydromorphine (1 mmol), Drierite (1 g), and Hg(CN)$_2$ (0.75 mmol) in dry acetonitrile (5 mL) is stirred at room temperature for 1 h. After 1 h, 2,3,4,6-tetra-O-acetyl-α-D-glucopyranosyl bromide (1.5 mmol) is added, and the resulting suspension is stirred for 3–4 days with the exclusion of moisture. The reaction mixture is filtered, concentrated, diluted with dichloromethane, and washed with aqueous 1 M potassium bromide solution. The resulting organic phase is dried, concentrated, and purified using chromatography to provide 3-acetyl 6-β-O-glucosyldihydromorphine. The 3-acetyl 6-β-O-glucosyldihydromorphine is dissolved in methanol (5 mL) and the solution is made alkaline by the addition of 1 M sodium methoxide. The resulting alkaline solution is allowed to stand for about 3 h and is neutralized with Amberlite IR 120 resin (Aldrich Chemical Co., Milwaukee, Wis.), avoiding a large excess of the resin. The solvent is then removed, optionally under reduced pressure, and the resulting residue is purified using column chromatography to provide 6-β-O-glucosyldihydromorphine.

Example 5

6-β-O-Glucosyldihydroisomorphine

A mixture of 3-acetyl dihydroisomorphine (1 mmol), Drierite (1 g), and Hg(CN)$_2$ (0.75 mmol) in dry acetonitrile (5 mL) is stirred at room temperature for 1 h. After 1 h, 2,3,4,6-tetra-O-acetyl-α-D-glucopyranosyl bromide (1.5 mmol) is added, and the resulting suspension is stirred for 3–4 days with the exclusion of moisture. The reaction mixture is filtered, concentrated, diluted with dichloromethane, and washed with aqueous 1 M potassium bromide solution. The resulting organic phase is dried, concentrated, and purified using chromatography to provide 3-acetyl 6-β-O-glucosyldihydroisomorphine. The 3-acetyl 6-β-O-glucosyldihydroisomorphine is dissolved in methanol (5 mL), and the resulting solution is made alkaline by the addition of 1 M sodium methoxide. The alkaline solution is allowed to stand for about 3 h and is neutralized with Amberlite IR 120 resin (Aldrich Chemical Co., Milwaukee, Wis.), avoiding a large excess of the resin. The solvent is removed, optionally under reduced pressure, and the resulting residue is purified using column chromatography to afford 6-β-O-glucosyldihydroisomorphine.

Example 6

Opioid-Receptor Binding of 6-O-Glucosylhydromorphone and 6-O-Glucosyldihydromorphine The binding affinity of hydromorphone, dihydromorphine, dihydroisomorphine-6-glucoside, hydromorphone-3-glucoside and morphine sulfate to delta-, kappa- and mu-receptors was determined using a conventional radio-ligand dose-displacement assay, wherein each compound's ability to inhibit radio-ligand binding was determined by measuring the amount of radio-ligand bound to the receptor at varying concentrations of the compound (See, e.g., H. Kong et al., *Proc. Natl. Acad. Sci.* 91:8042–06 (1994) and K. Raynor et al., *Mol. Pharmacol.,* 45(2):330–4 (1994)).

Delta-Receptor Binding: To determine the binding affinity of the compounds to delta opiod receptors, the following radio-ligand dose-displacement assay was used. The assay involved using 0.2 nM [$^3$H]-naltrindole (33.0 Ci/mmol) (Nen Life Science Products, Inc., Boston, Mass.) as the radio-ligand and 10–20 μg of membrane protein containing recombinant delta opiod receptor expressed in CHO-K1 cells (Receptor Biology Inc., Beltsville, Md.), in a final volume of 200 μL of binding buffer (5 mM MgCl$_2$, 5% dimethylsulfoxide (DMSO), 50 mM Tris HCl, pH 7.4). Naltriben (K$_1$=1.1 nM) was used as the reference compound and the positive control. Non-specific binding was determined using 25 μM unlabeled naloxone. All reactions were performed in 96-well polypropylene plates for 2 hours at room temperature. The reactions were terminated by rapid vacuum filtration onto a 96-well Unifilter GF/C filter plate with glass fiber filters (Packard Bioscience Company, Meriden, Conn.); the glass filters were pre-soaked in 0.5% polyethyleneimine (Sigma Chemical Co., St. Louis, Mo.). Following vacuum filtration the glass fiber filters were washed five times with 200 mL of ice-cold binding buffer and dried at 50° C. for 2–3 hours. After drying, 50 μL of Microscint scintillation cocktail (Packard Bioscience Company, Meriden, Conn.) was added to each well, and the radioactivity in each well was counted using a Packard Top-Count (Packard Bioscience Company, Meriden, Conn.) for 1 minute per well.

Data for the amount of radio-ligand bound to the filter at each concentration of hydromorphone, dihydromorphine, dihydroisomorphine-6-glucoside, hydromorphone-3-glucoside, and morphine sulfate were used to generate inhibition curves. Binding-affinity data for delta receptors, as measured by inhibition constant (Ki), were obtained using curve-fitting functions in GraphPad PRISM v. 3.0 (Graphpad Software Inc., San Diego, Calif.) and are reported in Table 1.

TABLE 1

Delta-Receptor Binding Affinity

| Compound | Ki (nm) |
|---|---|
| Hydromorphone | 172 |
| Dihydromorphine | 212 |
| Dihydroisomorphine-6-glucoside | 868 |
| Hydromorphone-3-glucoside | 4500 |
| Morphine Sulfate | 284 |

Kappa-Receptor Binding: To determine the binding affinity of the above compounds for kappa opioid receptors, the following radio-ligand dose-displacement assay was used. The assay involved using 0.15 nM [$^3$H]-bremazocine (26.5 Ci/mmol) (Nen Life Science Products, Inc.) as the radio-ligand and 10–20 μg of membrane protein containing recombinant kappa opiod receptor expressed in HEK 293 cells (Receptor Biology Inc) in a final volume of 200 μL of binding buffer (5% DMSO, 50 mM Tris HCl, pH 7.4). Naltriben ($K_i$=2.4 nM) was used as the reference compound and the positive control Non-specific binding was determined using 10 μM unlabeled naloxone. All reactions were performed in 96-well polypropylene plates for 2 hours at room temperature. The reactions were terminated by rapid vacuum filtration onto a 96-well Unifilter GF/C filter plate with glass fiber filters (Packard Bioscience Company); the glass filters were pre-soaked in 0.5% polyethyleneimine (Sigma Chemical Co. Inc.). Following vacuum filtration the glass fiber filters were washed five times with 200 mL of ice-cold binding buffer and dried at 50° C. for 2–3 hours. After drying, 50 μL of Microscint scintillation cocktail (Packard Bioscience Company) was added to each well and the radioactivity in each well counted using a Packard Top-Count (Packard Bioscience Company) for 1 minute per well.

Data for the amount of radio-ligand bound to the filter at each concentration of hydromorphone, dihydromorphine, dihydroisomorphine-6-glucoside, hydromorphone-3-glucoside, and morphine sulfate were used to generate inhibition curves. Binding-affinity data for kappa receptors, as measured by inhibition constant (Ki), were obtained using curve-fitting functions in GraphPad PRISM, v. 3.0 (Graphpad Software Inc., San Diego, Calif.) and are reported in Table 2.

TABLE 2

Kappa-Receptor Binding Affinity

| Compound | Ki (nm) |
|---|---|
| Hydromorphone | 99 |
| Dihydromorphine | 38 |
| Dihydroisomorphine-6-glucoside | 440 |
| Hydromorphone-3-glucoside | 2400 |
| Morphine sulfate | 268 |

Mu-Receptor Binding: To determine the binding affinity of the above compounds for the mu opioid receptor, the following radio-ligand dose-displacement assay was used. The assay involved using 0.2 nM [$^3$H]-diprenorphine (50.0 Ci/mmol) (commercially available from Nen Life Science Products, Inc.) as the radio-ligand and 15–20 μg of membrane protein containing recombinant mu-opioid receptor expressed in CHO-K1 cells (commercially available from Receptor Biology Inc.) in a final volume of 200 μL of binding buffer (10 mM mgCl$_2$, 1 mM EDTA, 5% DMSO, 50 mM Tris HCl, pH 7.4). Naloxone (K, of 3.1 nM) was used as the reference compound and the positive control Non-specific binding was determined using 100 nM unlabeled naloxone. All reactions were performed in 96-well polypropylene plates for 2 hours at room temperature. The reactions were terminated by rapid vacuum filtration onto a 96-well Unifilter GF/C filter plate with glass fiber filters (Packard Bioscience Company); the glass filters were pre-soaked in 0.5% polyethyleneimine (Sigma Chemical Company Inc.). Following vacuum filtration the glass fiber filters were washed five times with 200 mL of ice-cold binding buffer and dried at 50° C. for 2–3 hours. After drying, 50 μL of Microscint scintillation cocktail (Packard Bioscience Company) was added to each well and the radioactivity in each well counted using a Packard Top-Count (Packard Bioscience Company) for 1 minute per well.

Data for the amount of radio-ligand bound to the filter at each concentration of hydromorphone, dihydromorphine, dihydroisomorphine-6-glucoside, hydromorphone-3-glucoside, and morphine sulfate were used to generate inhibition curves. Binding-affinity data for the mu receptor, as measured by inhibition constant (Ki), were obtained using curve-fitting functions in GraphPad PRISM, v. 3.0 (Graphpad Software Inc., San Diego, Calif.) and are reported in Table 3.

TABLE 3

Mu-Receptor Binding Affinity

| Compound | Ki (nm) |
|---|---|
| Hydromorphone | 0.26 |
| Dihydromorphine | 0.39 |
| Dihydroisomorphine-6-glucoside | 4.7 |
| Hydromorphone-3-glucoside | 51 |
| Morphine sulfate | 14.3 |

Summary: Table 4 provides a summary of the binding-affinity data, as measured by the inhibition constants ($K_i$), for hydromorphone, dihydromorphine, dihydroisomorphine-6-glucoside, and hydromorphone-3-glucoside for delta, kappa, and mu opioid receptors.

TABLE 4

Summary of Binding-Affinity Data

| Compound | Ki (nm) | | |
|---|---|---|---|
| | Delta | Kappa | Mu |
| Hydromorphone | 172 | 99 | 0.26 |
| Dihydromorphine | 212 | 38 | 0.39 |
| Dihydroisomorphine-6-glucoside | 868 | 440 | 4.7 |
| Hydromorphone-3-glucoside | 4500 | 2400 | 51 |
| Morphine sulfate | 284 | 268 | 14.3 |

The data in Table 4 show that dihydroisomorphine-6-glucoside and hydromorphone-3-glucoside, illustrative compounds of the invention, have high selectivity for mu opioid receptors, relative to delta and kappa opioid receptors. Moreover, this selectivity is higher than that of morphine sulfate. Accordingly, dihydroisomorphine-6-glucoside and hydromorphone-3-glucoside, illustrative compounds of the invention, are surprisingly and unexpectedly useful for treating or preventing pain in a patient, while avoiding the side effects that are associated with traditional opioid analgesic agents.

Example 7

Isolation and Identification of Hydromorphone Glucoside Metabolites

Hydromorphone was administered to subjects at various doses and plasma and urine samples were collected from the subjects at various times following administration of hydromorphone. Plasma and urine samples were pooled and analyzed using liquid chromatography—mass spectrometry (LC-MS).

Hydromorphone was also incubated with a suspension of human hepatocytes and then analyzed using liquid chromatography- mass spectrometry (LC-MS). Hepatocytes were isolated from liver tissue from a female donor. Liver tissue was processed into hepatocytes by collagenase-based digestion of connective tissue followed by manual and mechanical separation and washing with media according to the two-step collagenase perfusion procedure of Li, et al., *Isolation and Culturing Hepatocytes from Human Liver*, J. of Tissue Culture Methods, 14, 139–146 (1992). Isolated hepatocytes were counted to determine yield, and viability was measured using Trypan Blue exclusion. Only cells with>80% viability were used in the study.

Hepatocytes were then combined with incubation media in a suitable vessel such that after the addition of the hydromorphone hydrochloride the cell density was $2.0 \times 10^6$ cells/mL in a final volume of 10 mL. Hydromorphone hydrochloride was prepared as a 100x stock solution and diluted with incubation media to create a dosing solution that achieved a final concentration of 100 μg/mL when added to the hepatocyte suspension. A negative control (hepatocytes and incubation media) and a media control (hydromrphone in incubation media) were also prepared.

The hepatocyte suspension containing hydromorphone hydrochloride was incubated (100 mL) in a 150-mL beaker for 4 hours on a slowly rotating orbital shaker. The negative control and media control were incubated in 15-mL conical tubes (one tube per control, 1 mL/tube) for 4 hours on an orbital shaker. After the 4-hour incubation, the hydromorphone hydrochloride-containing sample was transferred to a 15-mL conical tube and centrifuged to separate the hepatocytes from the incubation media. The control samples were also centrifuged and the resulting supernatant fractions from both controls and the hepatocyte suspension containing hydromorphone hydrochloride were stored at <-70° C. until assayed by LC-MS. Incubations were conducted at 37° C., 95% air/5% carbon dioxide, and saturating humidity. The incubation media was Hanks balanced salts solution, i.e., dibasic sodium phosphate, D-glucose, monobasic potassium phosphate, potassium chloride, and sodium chloride.

The LC-MS system used to analyze the urine samples, plasma samples, and supernatant of the hepatocyte suspension consisted of a model HP 1050 pump (commercially available from Hewlett Packard of Wilmington, Del.) or a model 6200 pump (commercially available from Hitachi of San Jose, Calif.) and a HP 1050 autosampler (commercially available from Hewlett Packard of Wilmington, Del.) coupled to a Finnigan LCQ LC/MS$^n$ mass spectrometer (commercially available from Finnigan of San Jose, Calif.). Control of the autosampler and the pump was achieved using the LCQ Navigator software. An electrospray ESI probe was used for the analysis. The HPLC was equipped with a 2×300 mm, 10 μm, reverse phase μBondapak C-18 HPLC column equipped with a Guard-Pak insert (Waters; Milford, Pa.). The mobile phase was $CH_3OH/CH_3CN/H_2O$ (5:5:90) containing 10 mM $NH_4OAc$ and 0.1% AcOH. The flow rate was 0.3 mL/minute. Injection volumes were between 1 and 5 mL.

Before injecting samples onto the LC-MS system, the plasma, urine, and hepatocyte samples were subjected to a primary separation using a Waters C-18 Sep-Pak cartridge. After primary separation, the resulting eluents were evaporated to dryness and reconstituted with mobile phase. The components of each samples were separated on the HPLC and detected using the LCQ mass spectrometer. Different MS detection modes (MS, MS/MS, and MS/MS/MS) were used to determine the structure of each separated component. Identification of each component was made based on retention time; molecular weight; transition ions; MS, MS/MS, and MS/MS/MS fragmentation; and signal intensity.

Analysis of plasma and urine samples showed the presence of hydromorphone -3-glucoside and a second compound along with other known metabolites. The structure of hydromorphone-3-glucoside was verified by comparison to a synthetically prepared reference sample. Based on mass spectral data, the second compound was one of the following: dihydromorphine-3-glucoside, dihydroisomorphine-3-glucoside, dihydromorphine-6-glucoside, or dihydroisomorphine-6-glucoside. The retention time and mass spectral data for hydromorphone-3-glucoside and the second compound are provided in Table 5.

TABLE 5

Summary of LC/MS Analysis

| Metabolite | Retention Time (minutes) | MS | MS/MS | MS/MS/MS |
|---|---|---|---|---|
| Hydromorphone-3-glucoside | 7.6 | 448 | 286 | 185, 229, 243 |
| Second compound | 7.2 | 450 | 288 | 187, 213, 231 |

Analysis of the supernatant from the human liver hepatocytes also showed the presence of hydromorphone-3-glucoside and the second compound. These results demonstrate that hydromorphone is metabolized by humans to produce hydromorphone-3-glucoside and dihydromorphine-3-glucoside, dihydroisomorphine-3-glucoside, or dihydromorphine-6-glucoside.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. Nordihydromorphine-3-glucuronide or a pharmaceutically acceptable salt thereof.

2. Nordihydroisomorphine-3-glucuronide or a pharmaceutically acceptable salt thereof.

3. Norhydromorphone-3-glucuronide or a pharmaceutically acceptable salt thereof.

4. The 3-O-glucosylhydromorphone or pharmaceutically acceptable salt thereof in isolated and purified form.

5. The 3-O-glucosyldihydroisomorphine or pharmaceutically acceptable salt thereof in isolated and purified form.

6. The 6-O-glucosyldihydroisomorphine or pharmaceutically acceptable salt thereof in isolated and purified form.

7. The 3-O-glucosyldihydromorphine or pharmaceutically acceptable salt thereof in isolated and purified form.

8. The 6-O-glucosyldihydromorphine or pharmaceutically acceptable salt thereof in isolated and purified form.

9. The nordihydromorphinc-3-glucuronide or pharmaceutically acceptable salt thereof of claim 1 in isolated and purified form.

10. The nordihydroisomorphine-3-glucuronide or pharmaceutically acceptable salt thereof of claim 2 in isolated and purified form.

11. The norhydromorphone-3-glucuronide or pharmaceutically acceptable salt thereof of claim 3 in isolated and purified form.

12. The 3-O-glucosylhydromorphone or pharmaceutically acceptable salt thereof of claim 4 being a β-glycoside.

13. The 3-O-glucosyldihydroisomorphine or pharmaceutically acceptable salt thereof of claim 5 being a β-glycoside.

14. The 6-O-glucosyldihydroisomorphine or pharmaceutically acceptable salt thereof of claim 6 being a β-glycoside.

15. The 3-O-glucosyldihydromorphine or pharmaceutically acceptable salt thereof of claim 7 being a β-glycoside.

16. The 6-O-glucosyldihydromorphine or pharmaceutically acceptable salt thereof of claim 8 being a β-glycoside.

17. The nordihydromorphine-3-glucuronide or pharmaceutically acceptable salt thereof of claim 9 being a β-glycoside.

18. The nordihydroisomorphine-3-glucuronide or pharmaceutically acceptable salt thereof of claim 10 being a β-glycoside.

19. The norhydromorphone-3-glucuronide or pharmaceutically acceptable salt thereof of claim 11 being a β-glycoside.

20. A composition comprising an effective amount of the 3-O-glucosylhydromorphone or a pharmaceutically acceptable salt thereof of claim 4 and a pharmaceutically acceptable carrier or vehicle.

21. A composition comprising an effective amount of the 3-O-glucosyldihydroisomorphine or a pharmaceutically acceptable salt thereof of claim 5 and a pharmaceutically acceptable carrier or vehicle.

22. A composition comprising an effective amount of the 6-O-glucosyldihydroisomorphine or a pharmaceutically acceptable salt thereof claim 6 and a pharmaceutically acceptable carrier or vehicle.

23. A composition comprising an effective amount of the 3-O-glucosyldihydromorphine or a pharmaceutically acceptable salt thereof of claim 7 and a pharmaceutically acceptable carrier or vehicle.

24. A composition comprising an effective amount of the 6-O-glucosyldihydromorphine or a pharmaceutically acceptable salt thereof of claim 8 and a pharmaceutically acceptable carrier or vehicle.

25. A composition comprising an effective amount of the nordihydromorphine-3-glucuronide or a pharmaceutically acceptable salt thereof of claim 1 and a pharmaceutically acceptable carrier or vehicle.

26. A composition comprising an effective amount of the nordihydroisomorphine-3-glucuronide or a pharmaceutically acceptable salt thereof of claim 2 and a pharmaceutically acceptable carrier or vehicle.

27. A composition comprising an effective amount of the norhydromorphone-3-glucuronide or a pharmaceutically acceptable salt thereof of claim 3 and a pharmaceutically acceptable carrier or vehicle.

28. The composition of claim 20, wherein the 3-O-glucosylhydromorphone or pharmaceutically acceptable salt thereof is a β-glycoside.

29. The composition of claim 20, wherein the 3-O-glucosyldihydroisomorphin or pharmaceutically acceptable salt thereof is a β-glycoside.

30. The composition of claim 22, wherein the 6-O-glucosyldihydroisomorphine or pharmaceutically acceptable salt thereof is a β-glycoside.

31. The composition of claim 23, herein the 3-O-glucosyldihydromorphine or pharmaceutically acceptable salt thereof is a β-glycoside.

32. The composition of claim 24, wherein the 6-O-glucosyldihydromorphine or pharmaceutically acceptable salt thereof is a β-glycoside.

33. The composition of claim 25, wherein the nordihydromorphine-3-glucuronide or pharmaceutically acceptable salt thereof is a β-glycoside.

34. The composition of claim 26, wherein the nordihydroisomorphine-3-glucuronide or pharmaceutically acceptable salt thereof is a β-glycoside.

35. The composition of claim 27, wherein the norhydromorphone-3-glucuronide or pharmaceutically acceptable salt thereof is a β-glycoside.

36. A method for treating pain in a patient, comprising administering to a patient in need thereof an effective amount of 3-0-glucosylhydromorphone or pharmaceutically acceptable salt thereof.

37. A method for treating pain in a patient, comprising administering to a patient in need thereof an effective amount of 3-0-glucosyldihydroisomorphine or pharmaceutically acceptable salt thereof.

38. A method for treating pain in a patient, comprising administering to a patient in need thereof an effective amount of 6-0-glucosyldihydroisomorphine or pharmaceutically acceptable salt thereof.

39. A method for treating pain in a patient, comprising administering to a patient in need thereof an effective amount of 3-0-glucosyldihydromorphine or pharmaceutically acceptable salt thereof.

40. A method for treating pain in a patient, comprising administering to a patient in need thereof an effective amount of 6-0-glucosyldihydromorphine or pharmaceutically acceptable salt thereof.

41. A method for treating pain in a patient, comprising administering to a patient in need thereof an effective amount of the nordihydromorphine-3-glucuronide or pharmaceutically acceptable salt thereof of claim 1.

42. A method for treating pain in a patient, comprising administering to a patient in need thereof an effective amount of the nordihydroisomorphine-3-glucuronide or pharmaceutically acceptable salt thereof of claim 2.

43. A method for treating pain in a patient, comprising administering to a patient in need thereof an effective amount of the norhydromorphone-3-giucuronide or pharmaceutically acceptable salt thereof of claim 3.

44. The method of claim 36, wherein the 3-O-glucosylhydromorphone or pharmaceutically acceptable salt thereof is a β-glycoside.

45. The method of claim 37, wherein the 3-O-glucosyldihydroisomorphine or pharmaceutically acceptable salt thereof is a β-glycoside.

46. The method of claim 36, wherein the 6-O-glucosyldihydroisomorphine or pharmaceutically acceptable salt thereof is a β-glycoside.

47. The method of claim 39, wherein the 3-O-glucosyldihydromorphine or pharmaceutically acceptable salt thereof is a β-glycoside.

48. The method of claim 40, wherein the 6-O-glucosyldihydromorphine or pharmaceutically acceptable salt thereof is a β-glycoside.

49. The method of claim 41, wherein the nordihydromorphine-3-glucuronide or pharmaceutically acceptable salt thereof is a β-glycoside.

50. The method of claim 42, wherein the nordihydroisomorphine-3-glucuronid-e or pharmaceutically acceptable salt thereof is a β-glycoside.

51. The method of claim 43, wherein the norhydromorphone-3-glucuronide or pharmaceutically acceptable salt thereof is a β-glycoside.

* * * * *

UNITED STATES PATENT AND TRADEMARK OFFICE
CERTIFICATE OF CORRECTION

PATENT NO.     : 6,740,641 B2
DATED          : May 25, 2004
INVENTOR(S)    : Gao et al.

It is certified that error appears in the above-identified patent and that said Letters Patent is hereby corrected as shown below:

Title page,
Item [54], Title, please change the title from "SUGAR DERIVATIVES OF HYDROMORPHONE, DIHYDROMORPHINE AND DIHYDROMORPHINE, COMPOSITIONS THEREOF AND USES FOR TREATING OR PREVENTING PAIN" to -- SUGAR DERIVATIVES OF HYDROMORPHONE, DIHYDROMORPHINE AND DIHYDROISOMORPHINE, COMPOSITIONS THEREOF AND USES FOR TREATING OR PREVENTING PAIN --

Column 34,
Lines 62, 64 and 66, please delete "The".

Column 35,
Lines 1 and 3, please delete "The".

Signed and Sealed this

Twenty-first Day of December, 2004

JON W. DUDAS
*Director of the United States Patent and Trademark Office*